United States Patent [19]

Zipplies et al.

[11] Patent Number: 5,068,245

[45] Date of Patent: * Nov. 26, 1991

[54] FUNGICIDAL N-SUBSTITUTED 3-ARYLPYRROLIDINE DERIVATIVES

[75] Inventors: Matthias Zipplies, Hirschberg; Hubert Sauter, Mannheim; Franz Roehl, Ludwigshafen; Walter Himmele, Walldorf; Eberhard Ammermann, Ludwigshafen; Ernst-Heinrich Pommer, Limburgerhof, all of Fed. Rep. of Germany

[73] Assignee: BASF Aktiengesellschaft, Ludwigshafen, Fed. Rep. of Germany

[ * ] Notice: The portion of the term of this patent subsequent to Nov. 26, 2008 has been disclaimed.

[21] Appl. No.: 251,243

[22] Filed: Sep. 30, 1988

[30] Foreign Application Priority Data

Sep. 30, 1987 [DE] Fed. Rep. of Germany ....... 3732930

[51] Int. Cl.$^5$ ................... A01N 43/36; A01N 43/08; A01N 43/28; C07D 207/06
[52] U.S. Cl. ..................................... 514/429; 514/63; 514/409; 514/422; 514/428; 548/406; 548/407; 548/517; 548/527; 548/575; 548/577; 548/570
[58] Field of Search ............... 548/406, 570, 575, 577, 548/407, 517, 527; 514/63, 428, 429, 409, 422

[56] References Cited

U.S. PATENT DOCUMENTS 4,301,284 11/1981 Buschmann et al. ............... 544/106
4,472,412 9/1984 Buschmann et al. ........... 548/578 X

FOREIGN PATENT DOCUMENTS 0182224 5/1986 European Pat. Off. .
0243940 11/1987 European Pat. Off. .
0244739 11/1987 European Pat. Off. .
2727482 1/1979 Fed. Rep. of Germany .

*Primary Examiner*—Joseph Paul Brust
*Attorney, Agent, or Firm*—Oblon, Spivak, McClelland, Maier & Neustadt

[57] ABSTRACT

N-Substituted 3-arylpyrrolidine derivatives of the formula

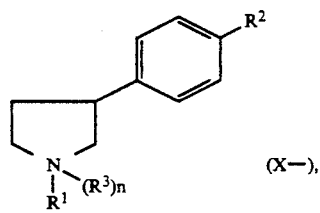

where
$R^1$ is 2,2-dimethylpropyl, 3,3-dimethylbutyl, 4,4-dimethylpentyl, 2,4,4-trimethylpentyl, 6-methylhept-2-yl, 3,5,5-trimethylhexyl, 6,10-dimethylundec-2-yl, 3-methylcyclohexyl, 3,3-dimethylcyclohexyl, 3,3,5-trimethylcyclohexyl, 3,3,5,5-tetramethylcyclohexyl, 4-methylcyclohexyl, 4-ethylcyclohexyl, 4-propylcyclohexyl, 4-isopropylcyclohexyl, 4-tert.-butylcyclohexyl, trans-4-tert.-butylcyclohexyl, 4(2-methylbut-2-yl)cyclohexyl, 4(2,4,4-trimethylpent-2-yl)-cyclohexyl, cyclododecanyl, $C_3$–$C_9$-trialkylsilyl-substituted $C_4$–$C_{12}$-cycloalkyl, 4-hydroxycyclohexyl, 4-hydroxy-3-methylcyclohexyl, 4-hydroxy-3,5-dimethylcyclohexyl, 4-hydroxy-3,3-dimethylcyclohexyl, 4-hydroxy-3,3,5-trimethylcyclohexyl, unsubstituted or hydroxy-, $C_1$–$C_9$-alkyl-, $C_1$–$C_5$-alkoxy- or $C_3$–$C_9$-trialkylsilyl-substituted $C_5$–$C_{12}$-cycloalkenyl,
$R^1$ is further bicycloalkyl,
$R^1$ is further 4-tert.-butyl-benzyl, 4-chlorobenzyl, 4-tert.-butoxybenzyl, 1,4-dioxaspiro[4,5]decan-8-yl,
5 to 7-membered heterocycloalkyl,
5 to 7-membered heterocycloalkylmethyl,
$R^2$ is alkyl, alkoxy or trialkylsilyl,
$R^3$ is alkyl, alkenyl, alkynyl or arylalkyl,
X- is a plant-tolerated anion,
n is 0 or 1, and plant-tolerated salts thereof, and fungicides containing these compounds.

11 Claims, No Drawings

FUNGICIDAL N-SUBSTITUTED 3-ARYLPYRROLIDINE DERIVATIVES

BACKGROUND OF THE INVENTION

1. Field of the Invention

The present invention relates to novel N-substituted 3-arylpyrrolidines, processes for their preparation, their use as fungicides, fungicides which contain the novel active ingredients and methods for controlling harmful fungi with these active ingredients.

2. Discussion of the Background

DE 27 27 482 discloses the following arylalkylpyrrolidine derivative as a compound having a fungicidal action. However, its action is unsatisfactory.

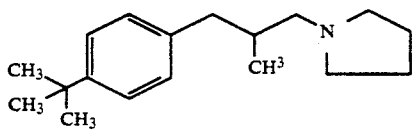

We have found that compounds of the formula I

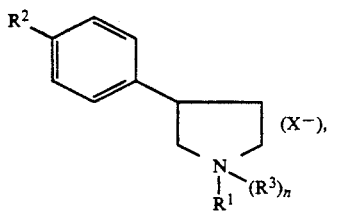

where $R^1$ is 2,2-dimethylpropyl, 3,3-dimethylbutyl, 4,4'-dimethylpentyl, 2,4,4-trimethylpentyl, 6-methylhept-2-yl, 3,5,5-trimethylhexyl, 6,10-dimethylundec-2-yl, 3-methylcyclohexyl, 3,3-dimethylcyclohexyl, 3,3,5-trimethylcyclohexyl, 3,3,5,5-tetramethylcyclohexyl, 4-methylcyclohexyl, 4-ethylcyclohexyl, 4-propylcyclohexyl, 4-isopropylcyclohexyl, 4-tert-butylcyclohexyl, trans-4-tert-butylcyclohexyl, 4-(2-methylbut-2-yl)-cyclohexyl, 4-(2,4,4-trimethylpent-2-yl)-cyclohexyl, cyclododecyl, $C_3$–$C_9$-trialkylsilyl-substituted $C_4$–$C_{12}$-cycloalkyl, 4-hydroxycyclohexyl, 4-hydroxy-3-methylcyclohexyl, 4-hydroxy-3,5-dimethylcyclohexyl, 4-hydroxy-3,3-dimethylcyclohexyl, 4-hydroxy-3,3,5-trimethylcyclohexyl, or $C_5$–$C_{12}$-cycloalkenyl which is unsubstituted or substituted by hydroxyl, $C_1$–$C_9$-alkyl, $C_1$–$C_5$-alkoxy or $C_3$–$C_9$-trialkylsilyl, or $R^1$ is furthermore $C_9$–$C_{11}$-bicycloalkyl which is unsubstituted or substituted by hydroxyl, $C_1$–$C_6$-alkyl, $C_1$–$C_5$-alkoxy, $C_3$–$C_9$-trialkylsilyl, acetoxy, benzoyloxy or benzyloxy, or $R^1$ is furthermore 4-tert-butylbenzyl, 4-chlorobenzyl, 4-tert-butoxybenzyl, 1,4-dioxaspiro[4,5]dec-8-yl, a 5-membered to 7-membered heterocycloalkyl having 1 or 2 hetero atoms from the group consisting of oxygen and/or sulfur, a 5-membered to 7-membered heterocycloalkylmethyl having 1 or 2 hetero atoms from the group consisting of oxygen and/or sulfur, or a $C_1$–$C_8$-alkyl-substituted 5-membered to 7-membered heterocycloalkyl or heterocycloalkylmethyl having 1 or 2 hetero atoms from the group consisting of oxygen and/or sulfur, $R^2$ is $C_3$–$C_{10}$-alkyl, $C_3$–$C_8$-alkoxy or $C_3$–$C_9$-trialkylsilyl, $R^3$ is $C_1$–$C_5$-alkyl, $C_3$–$C_6$-alkenyl, $C_3$–$C_6$-alkynyl or $C_7$–$C_{10}$-arylalkyl, X- is a plant-tolerated anion and n is 0 or 1, and their plant-tolerated salts possess an excellent fungicidal action coupled with good toleration by plants.

Salts are understood as salts having a plant-tolerated anion X- of any inorganic or organic acid, for example of hydrochloric acid, hydrofluoric acid, hydrobromic acid, sulfuric acid, phosphoric acid, hydriodic acid, dodecylbenzenesulfonic acid, formic acid, alkylcarboxylic acids, acetic acid, propionic acid, palmitic acid, perfluoroheptanoic acid, oxalic acid, malonic acid, benzoic acid, malic acid, dodecylsulfuric acid, glycerol-2-phosphoric acid, methylsulfuric acid, methanesulfonic acid, p-toluenesulfonic acid or nitric acid, for example the bisulfate and dihydrogen phosphate salts.

DETAILED DESCRIPTION OF THE PREFERRED EMBODIMENTS

The novel N-substituted 3-arylpyrrolidines of the formula I contain chiral centers. They are obtained in their preparation in general as racemates or may be obtained as diastereomer mixtures.

In the case of some of the novel compounds, pure diastereomeric compounds can be isolated, for example, by distillation, column chromatography or on the basis of solubility differences. Pure enantiomeric compounds can be obtained, for example, by resolution of the racemate with a chiral auxiliary reagent by a known method, for example via diastereomeric salts.

Regarding the use of the novel N-substituted 3-arylpyrrolidines as fungicides, the diastereomers and the enantiomers as well as their stereoisomer mixtures obtained in the synthesis are suitable. They all form subjects of the invention.

$R^1$ is, for example, 2,2-dimethylpropyl, 3,3-dimethylbutyl, 4,4-dimethylpentyl, 2,4,4-trimethylpentyl, 6-methylhept-2-yl, 3,5,5-trimethylhexyl, 6,10-dimethylundec-2-yl, 3-methylcyclohexyl, 3,3-dimethylcyclohexyl, 3,3,5-trimethylcyclohexyl, 3,3,5,5-tetramethylcyclohexyl, 4-methylcyclohexyl, 4-ethylcyclohexyl, 4-propylcyclohexyl, 4-isopropylcyclohexyl, trans-4-isopropylcyclohexyl, 4-tert-butylcyclohexyl, trans-4-tert-butylcyclohexyl, 4-(2-methylbut-2-yl)-cyclohexyl, 4-(2,4,4-trimethylpent-2-yl)-cyclohexyl, cyclododecyl, $C_3$–$C_9$-trialkylsilyl-substituted $C_4$–$C_{12}$-cycloalkyl, e.g. 4-trimethylsilylcyclohexyl, 4-hydroxycyclohexyl, 4-hydroxy-3-methylcyclohexyl, 4-hydroxy-3,5-dimethylcyclohexyl, 4-hydroxy-3,3-dimethylcyclohexyl, 4-hydroxy-3,3,5-trimethylcyclohexyl; $C_5$–$C_{12}$-cycloalkenyl which may be substituted by one or more of the following radicals: hydroxyl, $C_1$–$C_9$-alkyl, $C_1$–$C_5$-alkoxy or $C_3$–$C_9$-trialkylsilyl, e.g. 4-tert-butylcyclohexenyl, 4-tert-butoxycyclohexenyl or 4-trimethylsilylcyclohexenyl;

$C_9$–$C_{11}$-bicycloalkyl which may be substituted by one or more of the following radicals: hydroxyl, $C_1$–$C_6$-alkyl, $C_1$–$C_5$-alkoxy, $C_3$–$C_9$-trialkylsilyl, acetoxy, benzyloxy or benzoyloxy, e.g. [4.3.0]bicyclononyl, decalyl, 9-methyl-2-decalyl, 5,9-dimethyl-2-decalyl, 5,5,9-trimethyl-2-decalyl, 6-hydroxy-2-decalyl, 6-benzoyloxy-2-decalyl, 7-hydroxy-2-decalyl, 6-hydroxy-9-methyl-2-decalyl, 6-hydroxy-5,9-dimethyl-2-decalyl, 6-hydroxy-5,5,9-trimethyl-2-decalyl or 6-benzoyloxy-5,9-dimethyl-2-decalyl;

5-membered to 7-membered heterocycloalkyl having 1 or 2 hetero atoms from the group consisting of oxygen and sulfur, e.g. tetrahydropyranyl, tetrahydrothiopyranyl or dioxanyl;

5-membered to 7-membered heterocycloalkylmethyl having 1 or 2 hetero atoms from the group consisting of oxygen and sulfur, e.g. tetrahydropyranylmethyl or dioxanylmethyl; $C_1$-$C_8$-alkyl-substituted 5-membered to 7-membered heterocycloalkyl or heterocycloalkylmethyl having 1 or 2 hetero atoms from the group consisting of oxygen and sulfur, e.g. tetrahydropyranylmethyl, dioxanylmethyl, 3,5-dimethyldioxan-2-ylmethyl, diethyldioxan-2-ylmethyl, 2-isopropyl-1,3-dioxan-5-yl or 2-tert-butyl-1,3-dioxan-5-yl, and $R^1$ is furthermore 4-tert-butylbenzyl, 4-chlorobenzyl, 4-tert-butoxybenzyl or 1,4-dioxaspiro[4.5]dec-8-yl.

$R^2$ is, for example, branched or straight-chain $C_3$-$C_{10}$-alkyl, e.g. propyl, isopropyl, sec-butyl, tert-butyl, 2-methylbut-2-yl or 2,4,4-trimethylpent-2-yl, branched or straight-chain $C_3$-$C_8$-alkoxy, e.g. propoxy, isopropoxy, butoxy or tert-butoxy, or $C_3$-$C_9$-trialkylsilyl, e.g. trimethylsilyl.

$R^3$ is, for example, $C_1$-$C_5$-alkyl, e.g. methyl, ethyl, propyl, butyl or pentyl, $C_3$-$C_6$-alkenyl, e.g. allyl or methallyl, $C_3$-$C_6$-alkynyl, e.g. propargyl, or $C_7$-$C_{10}$-arylalkyl, e.g. benzyl or phenylethyl.

The compounds of the formula I can be prepared, for example, by

N-alkylation of pyrrolidines of the formula II where $R^2$ is alkyl, by Friedel-Crafts alkylation of N-alkylated phenylpyrrolidines of the formula VI reactions which synthesize the 5-membered heterocycle, followed by a reduction.

The processes are described below: Introduction of the radical $R^1$ a) Reaction of a pyrrolidine derivative II with a compound $R^1$-X under basic conditions.

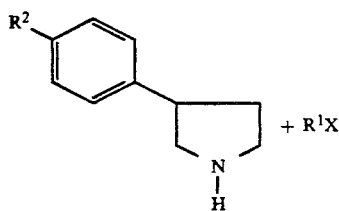

X is, for example, chlorine, bromine, iodine, methanesulfonyl, benzenesulfonyl or p-toluenesulfonyl or the radicals corresponding to the abovementioned anions X-.

The reaction is carried out, for example, at 40°-200° C. in the presence or absence of an inert solvent. Preferred bases are inorganic bases, for example potassium hydroxide, sodium hydroxide, lithium hydroxide, sodium hydride, potassium carbonate and sodium carbonate. Other suitable bases are organic bases, such as triethylamine, dicyclohexylamine and diisopropylamine. The reaction can also be carried out using an excess of the pyrrolidine derivative II.

b) Reaction of a carbonyl compound III

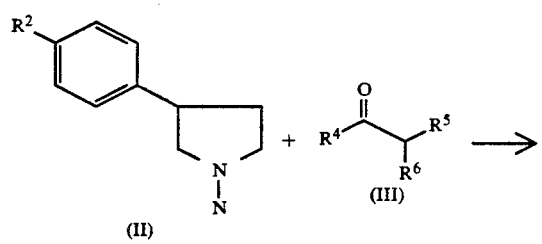

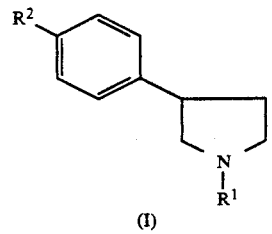

where $R^4$, $R^5$ and $R^6$ are defined such that the radical

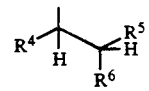

in its entirety corresponds to the radical $R^1$, with a pyrrolidine derivative II with simultaneous or subsequent reduction or hydrogenation.

b$_1$) In the direct method for the preparation of the compound I, a mixture of II and III in the presence of a solvent, e.g. methanol, ethanol, propanol or isopropanol, which may contain up to 25% by volume of water, is reacted with sodium cyanoborohydride or sodium borohydride in the presence or absence of a metal salt, such as zinc-(II) chloride, cadmium(II) chloride or magnesium(II) chloride, at 0°-100° C., preferably 20°-80° C., or with hydrogen in the presence of a solvent, e.g. methanol, ethanol, tetrahydrofuran or toluene, and of a hydrogenation catalyst, e.g. Raney nickel, platinum(IV) oxide, $Ru_2O_3$ or palladium on carbon, in an autoclave at 100°-150° C. until the pressure remains constant.

b$_2$) In the two-stage reaction, an enamine is prepared from the compounds II and III in a conventional manner under water-eliminating conditions and the product is then reduced using a noble metal catalyst, such as Raney nickel, Raney cobalt, $PtO_2$ or $Ru_2O_3$, preferably palladium on carbon, and hydrogen.

c) Where $R^2$ is $C_3$-$C_{10}$-alkyl, $R^2$ can be introduced into a phenylpyrrolidine derivative of the structure VI

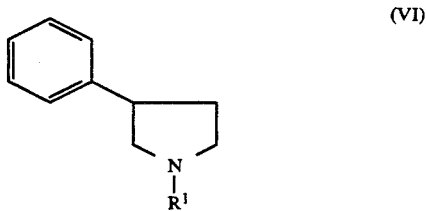

by reacting the said derivative, under acid catalysis, with an alkene of the structure Va

where $R^a$ to $R^d$ are defined such that the radical Vb in its entirety

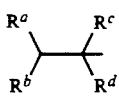

corresponds to the radical $R^2$, or with an alkyl halide $R^2$-X. Mineral acids, e.g. sulfuric acid, hydrochloric acid or hydrobromic acid, or Lewis acids, such as $AlCl_3$ or $SnCl_4$, are used, and the reaction is carried out while cooling with ice, for example at from $-10°$ to $+20°$ C.

d) Ring-synthesizing reactions

The compounds I can also be prepared by reacting a primary amine of the formula $R^1$-$NH_2$ with a compound VIIIa, VIIIb or VIIIc and then reducing the carbonyl group or groups.

In the reaction of dicarboxylic acids, succinic anhydrides and lactones having a 5-membered ring, the water of reaction is removed from the equilibrium either in a water separator using a suitable entraining agent or in the presence of a water-binding agent.

Suitable solvents for the water separation are relatively high boiling hydrocarbons, such as toluene, xylene, chlorobenzene or naphtha. Suitable water-binding agents are acetone and molecular sieves.

However, it is also possible to dispense with solvents. The reactions can be carried out at 100° C. or higher. If the reaction temperature cannot be reached under atmospheric pressure, the reaction is carried out in an autoclave under the autogenous pressure of the reaction mixture, at the required conversion temperature.

The dicarbonyl dihalides can be reacted at from $-20°$ to $+100°$ C., preferably from 0° to $+10°$ C., in the presence of a base which may additionally serve as a solvent, e.g. diisopropylamine, tributylamine, pyridine, picoline, triethylamine or dicyclohexylamine, or of a base, such as sodium carbonate, potassium carbonate or sodium bicarbonate, in the presence of an inert solvent, such as chloroform, dichloromethane or tetrahydrofuran.

The reaction of the amine derivatives $R^1$-$NH_2$ with a lactone derivative having a 5-membered ring (VIIIc, B=NH) takes place at elevated temperatures of from

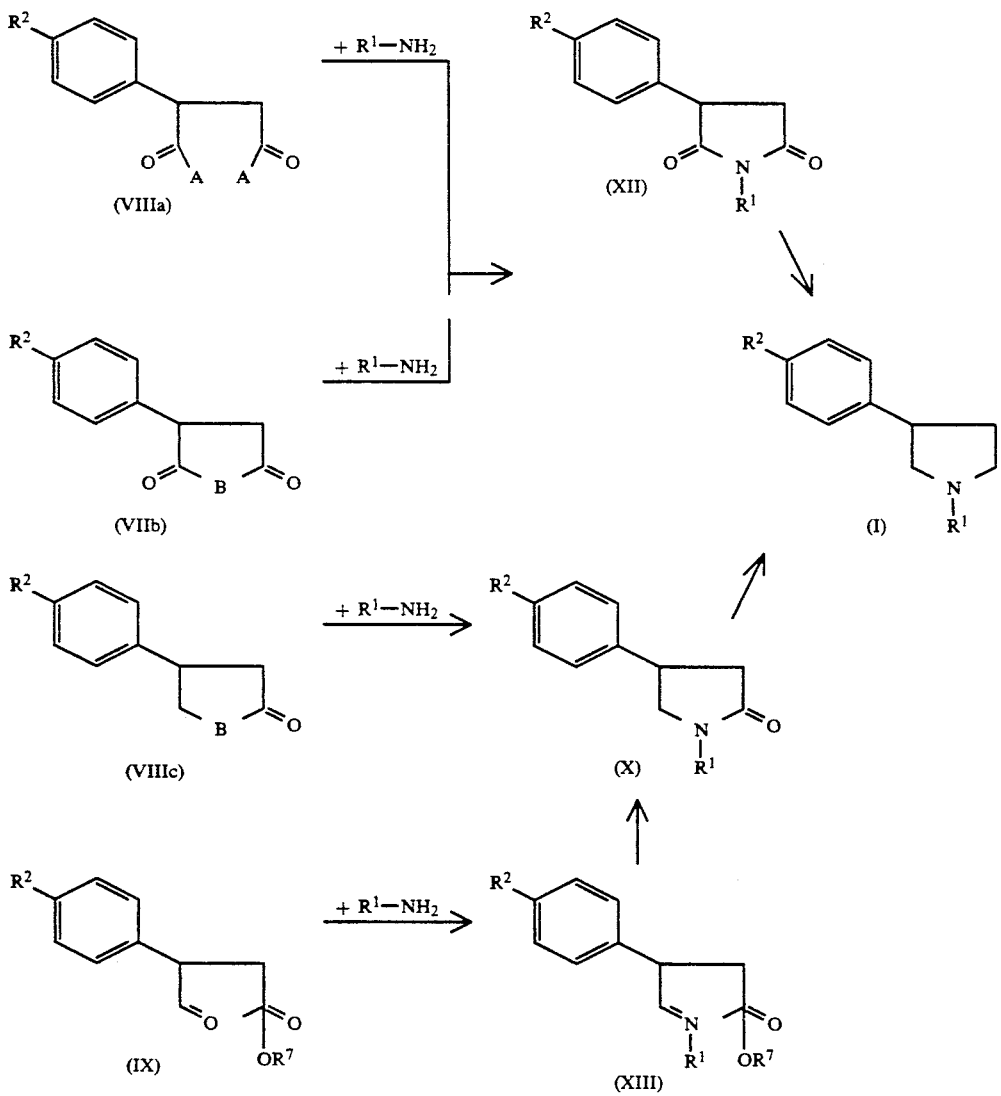

A = hydroxyl, alkoxy or halogen
B = O or NH
$R^7$ = alkyl

150° to 280° C., and the required reaction temperature can be obtained in an autoclave. The reaction can be carried out in an inert solvent, e.g. toluene, xylene, ethanol, isopropanol or cyclohexanol, or in the absence of a solvent.

The carbonyl compound can be reduced to the alkyl compound by reaction with a reducing agent at from −20° to +100° C., preferably from 0° to +60° C. Preferably used reducing agents are hydrides, such as lithium aluminum hydride or diborane.

The reduction can also be carried out under Wolff-Kishner reaction conditions or electrochemically.

Suitable solvents for the hydride reaction are ethers, such as diethyl ether, diisopropyl ether, methyl tert-butyl ether, tetrahydrofuran or dioxane, and hydrocarbons, such as xylene or toluene.

The 3-formylpropionate derivatives of the general structure IX can be reacted at 0°–100° C. with the amines $R^1$-$NH_2$ to give the Schiff's bases of the general structure XIII in the presence or absence of a water-eliminating agent, such as sodium sulfate, magnesium sulfate or a molecular sieve, or in a water separator using a suitable entraining agent.

Suitable solvents are chlorohydrocarbons, such as dichloromethane, ethers, such as tetrahydrofuran, and hydrocarbons, such as toluene or xylene.

The compounds XIII can be converted in a conventional manner using a reducing agent, such as sodium borohydride or lithium aluminum hydride, or with hydrogen over a catalyst, such as palladium/alumina or Raney nickel, into the pyrrolidone derivatives X. The latter can be reacted, as described above, with a reducing agent, e.g. lithium aluminum hydride, in ether or dioxane, to give the novel compounds I.

The present invention furthermore relates to a process for the preparation of the quaternary salts by reacting a pyrrolidine derivative of the formula I with a compound $R^3$-X.

X is, for example, chlorine, bromine, iodine, methanesulfonyl, p-toluenesulfonyl or methylsulfate. The reaction is carried out at 10°–200° C. in the presence or absence of an inert solvent. Suitable solvents are hydrocarbons, such as decalin, toluene or xylene, chlorohydrocarbons, such as chlorobenzene, ethers, such as tetrahydrofuran or dioxane, dipolar aprotic solvents, such as dimethyl sulfoxide, dimethylformamide, sulfolane, acetonitrile, and alcohols, such as methanol, ethanol, propanol, butanol or amyl alcohol; however, the reaction can also be carried out in the absence of a solvent. The counter-ion $X^-$ formed during the preparation can be exchanged for another suitable anion by means of an anion exchanger or by a reprecipitation reaction.

For example, 3-phenylpyrrolidine can be reacted with isobutylene in a chlorohydrocarbon, such as dichloromethane, carbon tetrachloride, tetrachloroethane or chlorobenzene, or another suitable solvent, such as carbon disulfide or nitrobenzene, under acid catalysis to give I ($R^2$=tert-butyl).

A mineral acid, e.g. sulfuric acid, is used as a catalyst and the reaction is carried out while cooling with ice at from −5° to +20° C.

The starting materials are known or can be prepared in a conventional manner.

The Examples which follow illustrate the preparation of the novel compounds.

PREPARATION EXAMPLES

Example 1

3-(4-tert-butylphenyl)-pyrrolidine 98 g (1 mole) of concentrated sulfuric acid were added dropwise to 29.4 g (0.2 mole) of 3-phenylpyrrolidine in 400 ml of carbon tetrachloride at 0°–5° C. After 15 minutes, 15.2 g (0.27 mole) of isobutylene were passed in gaseous form, the mixture was stirred for 1 hour at 0°–5° C. and hydrolysis was carried out with 400 ml of water at 20° C. The organic phase was separated off and the aqueous phase was extracted with twice 100 ml of dichloromethane. Working up of the organic phases gave 42 g of a crude product, which was fractionated under reduced pressure to give 13.4 g (33%) of a colorless oil of boiling point 84°–87° C./0.5 mbar.

Example 2

N-(4-tert-butylcyclohexyl)-3-(4-tert-butylphenyl)-pyrrolidine (compound No. 16)

15.4 g (100 millimoles) of 4-tert-butylcyclohexanone, 9.8 g (48 millimoles) of 3-(4-tert-butylphenyl)-pyrrolidine, 6.8 g (50 millimoles) of zinc(II) chloride and 6.3 g (100 millimoles) of sodium cyanoborohydride in 200 ml of absolute methanol were stirred for 48 hours at 22° C. The methanol was distilled off under reduced pressure and the residue was dissolved in dichloromethane and 5% strength sodium hydroxide solution.

Working up of the organic extract and fractionation under reduced pressure (175°–180° C./0.4 mbar) gave an isomer mixture, which was chromatographed over silica gel with hexane/methyl tert-butyl ether: N-(cis-4-tert-butylcyclohexyl)-3-(4-tert-butylphenyl)-pyrrolidine, mp. 58° C. (compound 16b): 2.3 g (14%). N-(trans-4-tert-butylcyclohexyl)-3-(4-tert-butylphenyl)-pyrrolidine, mp. 50°–55° C. (compound No. 16a): 2.5 g (15%).

The compounds below can be prepared in a similar manner.

TABLE 1

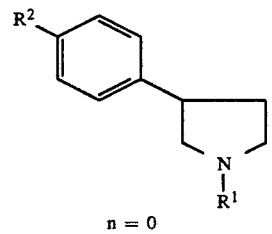

n = 0

| Comp. no. | $R^1$ | $R^2$ | bp. (°C./mbar) | IR absorption (cm$^{-1}$) [film] |
|---|---|---|---|---|
| 1 | 2,2-dimethyl-propyl | tert.-butyl | oil | 2954, 2905, 2867, 2780, 1478, 1464, 1394, 1361, 1141, 1121, |

TABLE 1-continued

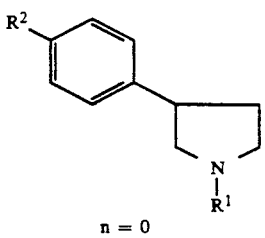

n = 0

| Comp. no. | R¹ | R² | bp. (°C./mbar) | IR absorption (cm⁻¹) [film] |
|---|---|---|---|---|
| 2 | 3,3-dimethyl-butyl | tert.-butyl | oil | 828, 572<br>2956, 2867, 1474, 1466, 1364, 1145, 828, 573 |
| 3 | 4,4-dimethyl-pentyl | tert.-butyl | 140/0.4 | |
| 4 | 2,4,4-trimethyl-pentyl | tert.-butyl | oil | 2956, 2909, 2868, 2787, 1476, 1465, 1393, 1383, 1364, 1268, 828, 573 |
| 5 | 6-methyl-hept-2-yl | tert.-butyl | 150–154/0.4 | |
| 6 | 3,5,5-trimethylhexyl | tert.-butyl | 152–155/0.4 | |
| 7 | 6,10-dimethyl-undec-2-yl | tert.-butyl | oil | 2956, 2927, 2867, 1464, 1377, 1366, 1169, 820 |
| 8 | 3-methyl-cyclohexyl | tert.-butyl | | |
| 9 | 3,3-dimethyl-cyclohexyl | tert.-butyl | 160–170/0.4 | |
| 10 | 3,3,5-trimethylcyclohexyl | tert.-butyl | | |
| 11 | 3,3,5,5-tetramethyl-cyclohexyl | tert.-butyl | | |
| 12 | 4-methyl-cyclohexyl | tert.-butyl | | |
| 13 | 4-ethyl-cyclohexyl | tert.-butyl | | |
| 14 | 4-propyl-cyclohexyl | tert.-butyl | | |
| 15 | 4-isopropyl-cyclohexyl | tert.-butyl | oil | 2958, 2934, 2865, 2777, 1464, 1449, 1369, 1366, 1152, 828 |
| 16 | 4-tert.-butyl-cyclohexyl | tert.-butyl | | |
| 16a | trans-4-tert.-butyl-cyclohexyl | tert.-butyl | mp 50–55 | |
| 16b | cis-4-tert.-butyl-cyclohexyl | tert.-butyl | mp 58 | |
| 17 | 4(2-methyl-but-2-yl)-cyclohexyl | tert.-butyl | | |
| 18 | 4(2,4,4-trimethyl-pent-2-yl)-cyclohexyl | tert.-butyl | | |
| 19 | cyclododecanyl | tert.-butyl | resin | 2932, 2863, 2849, 2776, 1472, 1446, 1362, 1121, 828, 572 |
| 20 | 4-trimethylsilyl-cyclohexyl | tert.-butyl | mp 75–79 | |
| 21 | 4-hydroxy-cyclohexyl | tert.-butyl | | |
| 22 | 4-hydroxy-3-methyl-cyclohexyl | tert.-butyl | | |
| 23 | 4-hydroxy-3,5-dimethyl-cyclohexyl | tert.-butyl | | |
| 24 | 4-hydroxy-3,3-dimethyl-cyclohexyl | tert.-butyl | | |
| 25 | 4-hydroxy-3,3,5-trimethyl-cyclohexyl | tert.-butyl | oil | 2961, 2868, 2778, 1476, 1460, 1363, 1338, 1058, 1038, 980 |
| 26 | 4-tert.-butyl-cyclohex-3-en-yl | tert.-butyl | | |
| 27 | 4-tert.-butyl-cyclohex-2-en-yl | tert.-butyl | | |
| 28 | 1-decalyl (cis/trans mixture) | tert.-butyl | | |
| 29 | 2-decalyl (cis/trans mixture) | tert.-butyl | 158–162/0.4 | |
| 30 | trans-2-decalyl (eq/ax. - substituted) | tert.-butyl | | |
| 31 | eq.-trans-2-decalyl | tert.-butyl | | |
| 32 | 6-hydroxy-2-decalyl | tert.-butyl | | |
| 33 | 7-hydroxy-2-decalyl | tert.-butyl | | |
| 34 | 2-decalylmethyl | tert.-butyl | | |
| 35 | 9-methyl-trans-2-decalyl | tert.-butyl | | |
| 36 | 5,9-dimethyl-trans-2-decalyl | tert.-butyl | | |
| 37 | 5,5,9-trimethyl-trans-2-decalyl | tert.-butyl | | |
| 38 | 6-hydroxy-9-methyl-2-decalyl | tert.-butyl | | |
| 39 | 6-hydroxy-5,9-dimethyl-2-decalyl | tert.-butyl | | |
| 40 | 6-hydroxy-5,5,9-trimethyl-2-decalyl | tert.-butyl | | |
| 41 | tetrahydropyran-4-yl | tert.-butyl | 125–130/0.4 | |
| 42 | tetrahydropyran-4-yl | tert.-butyl | | |
| 43 | dioxan-2-yl-methyl | tert.-butyl | | |
| 44 | tetrahydropyran-2-yl-methyl | tert.-butyl | | |
| 45 | tetrahydropyran-3-yl-methyl | tert.-butyl | | |
| 46 | 3,5-dimethyl-dioxan-2-yl-methyl | tert.-butyl | | |
| 47 | 3,5-diethyl-dioxan-2-yl-methyl | tert.-butyl | | |
| 48 | 3,6-diethyl-dioxan-2-yl-methyl | tert.-butyl | | |
| 49 | 2-isopropyl-1,3-dioxan-5-yl | tert.-butyl | | |
| 50 | 2-tert.-butyl-1,3-dioxan-5-yl | tert.-butyl | | |
| 51 | 4-tert.-butyl-cyclohexyl | tert.-butyl | | |
| 52 | trans-4-tert.-butyl-cyclohexyl | tert.-butyl | | |
| 53 | 4-tert.-butoxy-cyclohexyl | tert.-butyl | | |
| 54 | 4-tert.-butyl-benzyl | tert.-butyl | mp 89–94 | |
| 55 | 4-chlorobenzyl | tert.-butyl | oil | 2961, 2906, 2868, 2794, 1491, 1363, 1086, 1016, 830, 805 |
| 56 | 4-tert.-butoxy-benzyl | tert.-butyl | | |
| 57 | 1,4-dioxa-spiro[4,5]decan-8-yl | tert.-butyl | resin | 2954, 2874, 2783, 1382, 1367, |

TABLE 1-continued

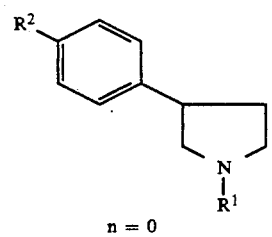

n = 0

| Comp. no. | R[1] | R[2] | bp. (°C./mbar) | IR absorption (cm[-1]) [film] |
|---|---|---|---|---|
| | | | | 1155, 1144, 1105, 1037, 923 |
| 58 | 3,3-dimethyl-butyl | 2-methyl-but-2-yl | | |
| 59 | 4,4-dimethyl-pentyl | 2-methyl-but-2-yl | | |
| 60 | 2,4,4-trimethyl-pentyl | 2-methyl-but-2-yl | | |
| 61 | 6-methyl-hept-2-yl | 2-methyl-but-2-yl | | |
| 62 | 6,10-dimethyl-undec-2-yl | 2-methyl-but-2-yl | | |
| 63 | 3-methyl-cyclohexyl | 2-methyl-but-2-yl | | |
| 64 | 3,3-dimethyl-cyclohexyl | 2-methyl-but-2-yl | | |
| 65 | 3,5,5-trimethyl-hexyl | 2-methyl-but-2-yl | | |
| 66 | 4-isopropyl-cyclohexyl | 2-methyl-but-2-yl | | |
| 67 | 4-tert.-butyl-cyclohexyl (isomer mixture) | 2-methyl-but-2-yl | | |
| 68 | trans-4-tert.-butyl-cyclohexyl | 2-methyl-but-2-yl | | |
| 69 | 4-trimethylsilylcyclohexyl | 2-methyl-but-2-yl | | |
| 70 | 4-hydroxy-cyclohexyl | 2-methyl-but-2-yl | | |
| 71 | 3,3,5-trimethyl-cyclohexyl | 2-methyl-but-2-yl | | |
| 72 | 2-decalyl | 2-methyl-but-2-yl | | |
| 73 | 6-hydroxy-2-decalyl | 2-methyl-but-2-yl | | |
| 74 | 5,5,9-trimethyl-2-decalyl | 2-methyl-but-2-yl | | |
| 75 | 6-hydroxy-5,9-dimethyl-2-decalyl | 2-methyl-but-2-yl | | |
| 76 | 6-hydroxy-5,5,9-Trimethyl-2-decalyl | 2-methyl-but-2-yl | | |
| 77 | 4-Isopropyl-cyclohexyl | 2,4,4-trimethyl-pent-2-yl | | |
| 78 | 3,3-dimethyl-cyclohexyl | 2,4,4-trimethyl-pent-2-yl | | |
| 79 | 3,3-dimethyl-butyl | 2,4,4-trimethyl-pent-2-yl | | |
| 80 | 4-tert.-butyl-cyclohexyl | 2,4,4-trimethyl-pent-2-yl | | |
| 81 | 4-trimethylsilyl-cyclohexyl | 2,4,4-trimethyl-pent-2-yl | | |
| 82 | 2-decalyl | 2,4,4-trimethyl-pent-2-yl | | |
| 83 | 6-hydroxy-2-decalyl | 2,4,4-trimethyl-pent-2-yl | | |
| 84 | 5,5,9-trimethyl-2-decalyl | 2,4,4-trimethyl-pent-2-yl | | |
| 85 | 6-hydroxy-5,9-dimethyl-decalyl | 2,4,4-trimethyl-pent-2-yl | | |
| 86 | 3,3-dimethylbutyl | tert.-butoxy | | |
| 87 | 4,4-dimethylpentyl | tert.-butoxy | | |
| 88 | 2,4,4-trimethyl-pentyl | tert.-butoxy | | |
| 89 | 6-methyl-hept-2-yl | tert.-butoxy | | |
| 90 | 3,5,5-trimethyl-hexyl | tert.-butoxy | | |
| 91 | 3-methyl-cyclohexyl | tert.-butoxy | | |
| 92 | 3,3-dimethyl-cyclohexyl | tert.-butoxy | | |
| 93 | 3,5,5-trimethyl-cyclohexyl | tert.-butoxy | | |
| 94 | 4-isopropyl-cyclohexyl | tert.-butoxy | | |
| 95 | 4-tert.-butyl-cyclohexyl | tert.-butoxy | | |
| 96 | 4-trimethylsilyl-cyclohexyl | tert.-butoxy | | |
| 97 | 2-decalyl | tert.-butoxy | | |
| 98 | 6-hydroxy-2-decalyl | tert.-butoxy | | |
| 99 | 5,5,9-trimethyl-decalyl | tert.-butoxy | | |
| 100 | 6-hydroxy-5,9-trimethyl-decalyl | tert.-butoxy | | |
| 101 | 4-hydroxy-3,3,5-trimethyl-cyclohexyl | tert.-butoxy | | |
| 102 | 4-tert.-butyl-cyclohexyl | trimethylsilyl | | |
| 103 | 3,3-dimethylcyclohexyl | trimethylsilyl | | |
| 104 | 2-decalyl | trimethylsilyl | | |
| 105 | 6-hydroxy-2-decalyl | trimethylsilyl | | |
| 106 | 3,3,5-trimethyl-cyclohexyl | trimethylsilyl | | |
| 107 | 5,5,9-trimethyl-2-decalyl | trimethylsilyl | | |

TABLE 2

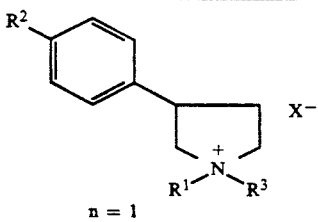

n = 1

| Comp. no. | R¹ | R² | R³ | X⁻ |
|---|---|---|---|---|
| 108 | 4-tert.-butyl-cyclohexyl | tert.-butyl | methyl | iodide |
| 109 | 4-tert.-butyl-cyclohexyl | tert.-butyl | methyl | chloride |
| 110 | 4-tert.-butyl-cyclohexyl | tert.-butyl | benzyl | chloride |
| 111 | 2-decalyl | tert.-butyl | methyl | iodide |
| 112 | 6-hydroxy-2-decalyl | tert.-butyl | methyl | iodide |
| 113 | 3,3-dimethyl-cyclohexyl | tert.-butyl | methyl | iodide |
| 114 | 5,5,9-trimethyl-2-decalyl | tert.-butyl | methyl | iodide |
| 115 | 2,2-dimethyl-propyl | tert.-butyl | methyl | iodide |
| 116 | 4,4-dimethyl-pentyl | tert.-butyl | methyl | iodide |
| 117 | 2,4,4-trimethyl-pentyl | tert.-butyl | methyl | iodide |
| 118 | 4-isopropyl-cyclohexyl | tert.-butyl | methyl | iodide |

In general terms, the novel compounds are extremely effective on a broad spectrum of phytopathogenic fungi, in particular those from the class consisting of the Ascomycetes and Basidiomycetes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:

*Erysiphe graminis* in cereals,
*Erysiphe cichoracearum* and *Sphaerotheca fuliginea* in cucurbits,
*Podosphaera leucotricha* in apples,
*Uncinula necator* in vines,
Puccinia species in cereals,
*Rhizoctonia solani* in cotton,
Ustilago species in cereals and sugar cane,
*Venturia inaequalis* (scab) in apples,
Helminthosporium species in cereals,
*Septoria nodorum* in wheat,
*Botrytis cinerea* (gray mold) in strawberries and grapes,
*Cercospora arachidicola* in groundnuts,
*Pseudocercosporella herpotrichoides* in wheat and barley,
*Pyricularia oryzae* in rice,
*Phytophthora infestans* in potatoes and tomatoes,
Fusarium and Verticillium species in various plants,
*Plasmopara viticola* in grapes,
Alternaria species in fruit and vegetables.

The compounds are applied by spraying or dusting the plants with the active ingredients, or treating the seeds of the plants with the active ingredients. They may be applied before or after infection of the plants or seeds by the fungi.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose.

The fungicides generally contain from 0.1 to 95, and preferably from 0.5 to 90, wt % of active ingredient. The application rates are from 0.02 to 3 kg or more of active ingredient per hectare, depending on the type of effect desired. The novel compounds may also be used for protecting materials, e.g., on Paecilomyces variotii.

Some of the novel compounds have a very good action on human-pathogenic fungi, such as *Trichophyton mentagrophytes* and *Candida albicans*.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. 90 parts by weight of compound no. 16a is mixed with 10 parts by weight of N-methyl-α-pyrrolidone. A mixture is obtained which is suitable for application in the form of very fine drops.

II. 20 parts by weight of compound no. 20 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 16a is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 20 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 16a is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 20 is intimately mixed with 97 parts by weight of particulate kaolin. A dust is obtained containing 3% by weight of the active ingredient.

VII. 30 parts by weight of compound no. 16a is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 20 is intimately mixed with 10 parts of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts by weight of compound no. 16a is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

In these application forms, the agents according to the invention may also be present together with other active ingredients, for example herbicides, insecticides, growth regulators, and fungicides, and may furthermore be mixed and applied together with fertilizers. Admixture with other fungicides frequently results in a greater fungicidal action spectrum.

The following list of fungicides with which the novel compounds may be combined is intended to illustrate possible combinations but not to impose any restrictions.

Examples of fungicides which may be combined with the novel compounds are:

sulfur,
dithiocarbamates and their derivatives, such as
ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate,
ammonia complex of zinc N,N'-propylenebisdithiocarbamate,
zinc N,N'-propylenebisdithiocarbamate and
N,N'-polypropylenebis(thiocarbamyl) disulfide;

nitro derivatives, such as dinitro(1-methylheptyl)-phenyl crotonate,
2-sec-butyl-4,6-dinitrophenyl 3,3-dimethylacrylate,
2-sec-butyl-4,6-dinitrophenyl isopropylcarbonate and diisopropyl 5-nitroisophthalate;

heterocyclic substances, such as 2-heptadecylimidazol-2-yl acetate,
2,4-dichloro-6-(o-chloroanilino)-s-triazine,
0,0-diethyl phthalimidophosphonothioate,
5-amino-1-[-bis-(dimethylamino)-phosphinyl]-3-phenyl-1,2,4-triazole,
2,3-dicyano-1,4-dithioanthraquinone,
2-thio-1,3-dithio[4,5-b]quinoxaline,
methyl 1-(butylcarbamyl)-2-benzimidazolecarbamate,
2-methoxycarbonylaminobenzimidazole,
2-(fur-2-yl)-benzimidazole,
2-(thiazol-4-yl)benzimidazole,
N-(1,1,2,2-tetrachloroethylthio)-tetrahydrophthalimide,
N-trichloromethylthiotetrahydrophthalimide,
N-trichloromethylthiophthalimide, N-dichlorofluoromethylthio-N',N'-dimethyl-N-phenyl-sulfuric acid diamide,
5-ethoxy-3-trichloromethyl-1,2,3-thiadiazole,
2-thiocyanatomethylthiobenzothiazole,
1,4-dichloro-2,5-dimethoxybenzene,
4-(2-chlorophenylhydrazono)-3-methyl-5-isoxazolone,
2-thiopyridine 1-oxide,
8-hydroxyquinoline and its copper salt,
2,3-dihydro-5-carboxanilido-6-methyl-1,4-oxathiyne,
2,3-dihydro-5-carboxanilido-6-methyl-1,4-oxathiyne 4,4-dioxide,
2-methyl-5,6-dihydro-4H-pyran-3-carboxanilide,
2-methylfuran-3-carboxanilide,
2,5-dimethylfuran-3-carboxanilide,
2,4,5-trimethylfuran-3-carboxanilide,
2,5-dimethyl-N-cyclohexylfuran-3-carboxamide,
N-cyclohexyl-N-methoxy-2,5-diethylfuran-3-carboxamide,
2-methylbenzanilide,
2-iodobenzanilide,
N-formyl-N-morpholine-2,2,2-trichloroethylacetal,
piperazine-1,4-diylbis-(1-(2,2,2-trichloroethyl)-formamide),
1-(3,4-dichloroanilino)-1-formylamino-2,2,2-trichloroethane,
2,6-methyl-N-tridecylmorpholine and its salts,
2,6-dimethyl-N-cyclododecylmorpholine and its salts,
N-[3-(p-tert.-butylphenyl)-2-methylpropyl]-cis-2,6-dimethylmorpholine,
N-[3-(p-tert.-butylphenyl)-2-methylpropyl]-piperidine,
1-[2-(2,4-dichlorophenyl)-4-ethyl-1,3-dioxolan-2-ylethyl]-1H-1,2,4-triazole,
1-[2-(2,4-dichlorophenyl)-4-n-propyl-1,3-dioxolan-2-ylethyl]-1H-1,2,4-triazole,
N-(n-propyl)-N-(2,4,6-trichlorophenoxyethyl)-N'-imidazolyl-urea,
1-(4-chlorophenoxy)-3,3-dimethyl-1-(1H-1,2,4-triazol-1-yl)-butan-2-one,
1-(4-chlorophenoxy)-3,3-dimethyl-1-(1H-1,2,4-triazol-1-yl)-butan-2-ol,
1-(4-phenylphenoxy)-3,3-dimethyl-1-(1H-1,2,4-triazol-1-yl)-2-butanol,
α-(2-chlorophenyl)-α-(4-chlorophenyl)-5-pyrimidinemethanol,
5-butyl-(2-dimethylamino-4-hydroxy-6-methylpyrimidine,
bis-(p-chlorophenyl)-3-pyridinemethanol,
1,2-bis-(3-ethoxycarbonyl-2-thioureido)-benzene,
1,2-bis-(3-methoxycarbonyl-2-thioureido)-benzene, and various fungicides, such as dodecylguanidine acetate,
3-[3-(3,5-dimethyl-2-oxycyclohexyl)-2-hydroxyethyl]-glutaramide, hexachlorobenzene,
DL-methyl-N-(2,6-dimethylphenyl)-N-fur-2-yl alanate,
methyl DL-N-(2,6-dimethylphenyl)-N-(2'-methoxyacetyl)-alanate,
N-(2,6-dimethylphenyl)-N-chloroacetyl-DL-2-aminobutyrolactone,
methyl DL-N-(2,6-dimethylphenyl)-N-(phenylacetyl)-alanate,
5-methyl-5-vinyl-3-(3,5-dichlorophenyl)-2,4-dioxo-1,3-oxazolidine,
3-[3,5-dichlorophenyl]-5-methyl-5-methoxymethyl-1,3-oxazolidine-2,4-dione,
3-(3,5-dichlorophenyl)-1-isopropylcarbamylhydantoin,
N-(3,5-dichlorophenyl)-1,2-dimethylcyclopropane-1,2-dicarboximide,
2-cyano-[N-(ethylaminocarbonyl)-2-methoximino]-acetamide,
1-[2-(2,4-dichlorophenyl)-pentyl]-1H-1,2,4-triazole,
2,4-difluoro-α-(1H-1,2,4-triazol-1-ylmethyl)-benzhydryl alcohol,
N-(3-chloro-2,6-dinitro-4-trifluoromethylphenyl)-5-trifluoromethyl-3-chloro-2-aminopyridine, and
1-((bis-(4-fluorophenyl)-methylsilyl)-methyl)-1H-1,2,4-triazole.

USE EXAMPLES

The agent used for comparison purposes was N-2-methyl-3-(p-tert-butylphenyl)-propylpyrrolidine (A) disclosed in DE-2,727,482.

Use Example 1

Action on *Botrytis cinerea* in Paprika

Paprika seedlings of the "Neusiedler Ideal Elite" variety were sprayed, after 4 to 5 leaves were well developed, to runoff with aqueous suspensions containing (dry basis) 80% of active ingredient and 20% of emulsifier. After the sprayed-on layer had dried, the plants were sprinkled with a conidial suspension of the fungus *Botrytis cinerea*, and placed at 22° to 24° C. in a chamber of high humidity. After 5 days, the disease had spread to such a great extent on the untreated plants that the necroses covered the major portion of the leaves.

The results show that active ingredients 16a and 20, when applied as 0.05% spray liquors, had a better fungicidal action (97%) than prior art comparative compound A (50%).

Use Example 2

Action on *Plasmopara viticola*

Leaves of potted vines of the Müller-Thurgau variety were sprayed with aqueous suspensions containing (dry basis) 80% of active ingredient and 20% of emulsifier. To assess the duration of action, the plants were set up, after the sprayed-on layer had dried, for 8 days in the greenhouse. Then the leaves were infected with a zoospore suspension of *Plasmopara viticola*. The plants were first placed for 48 hours in a water vaporsaturated chamber at 24° C. and then in a greenhouse for 5 days at from 20° to 30° C. To accelerate and intensify the sporangiophore discharge, the plants were then again placed in the moist chamber for 16 hours. The extent of fungus attack was then assessed on the undersides of the leaves.

The results show that active ingredients 16a and 20, when applied as 0.05 wt % spray liquors, had a better fungicidal action (97%) than prior art comparative agent A (60%).

We claim:

1. N-Substituted 3-arylpyrrolidine derivatives of the formula I

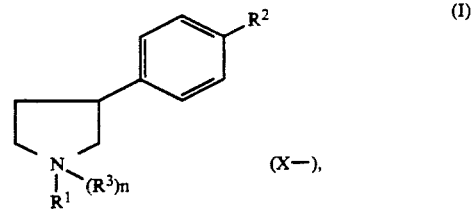

where
R$^1$ is 2,2-dimethylpropyl, 3,3-dimethylbutyl, 4,4-dimethylpentyl, 2,4,4-trimethylpentyl, 6-methylhept-2-yl, 3,5,5-trimethylhexyl, 6,10-dimethylundec-2-yl, 3-methylcyclohexyl, 3,3-dimethylcyclohexyl, 3,3,5-trimethylcyclohexyl, 3,3,5,5-tetramethylcyclohexyl, 4-methylcyclohexyl, 4-ethylcyclohexyl, 4-propylcyclohexyl, 4-isopropylcyclohexyl, 4-tert.-butylcyclohexyl, 4-(2-methylbut-2-yl)cyclohexyl, 4-(2,4,4-trimethylpent-2-yl)-cyclohexyl, cyclododecanyl, C$_3$-C$_9$-trialkylsilyl-substituted C$_4$-C$_{12}$-cycloalkyl, 4-hydroxycyclohexyl, 4-hydroxy-3-methylcyclohexyl, 4-hydroxy-3,5-dimethylcyclohexyl, 4-hydroxy-3,3-dimethylcyclohexyl, 4-hydroxy-3,3,5-trimethylcyclohexyl, unsubstituted or hydroxy-, C$_1$-C$_9$-alkyl-, C$_1$-C$_5$-alkoxy- or C$_3$-C$_9$-trialkylsilyl-substituted C$_5$-C$_{12}$-cycloalkenyl, R$^1$ is further C$_9$-C$_{11}$-bicycloalkyl which is unsubstituted or substituted by hydroxy, C$_1$-C$_6$-alkyl, C$_1$-C$_5$-alkoxy, C$_3$-C$_9$-trialkylsilyl, acetoxy, benzoyloxy or benzyloxy, R$^1$ is further 4-tert.-butyl-benzyl, 4-chlorobenzyl, 4-tert.-butoxybenzyl, 1,4-dioxaspiro[4,5]decan-8-yl, 5 to 7-membered heterocycloalkyl having 1 or 2 heteroatoms selected from the group consisting of oxygen and sulfur, 5 to 7-membered heterocycloalkylmethyl having 1 or 2 heteroatoms selected from the group consisting of oxygen and sulfur, C$_1$-C$_8$-alkyl-substituted 5 to 7-membered heterocycloalkyl or heterocycloalkylmethyl having 1 or 2 heteroatoms selected from the group consisting of oxygen and sulfur, R$^2$ is C$_3$-C$_8$-alkoxy or C$_3$-C$_9$-trialkylsilyl, R$^3$ is C$_1$-C$_5$-alkyl, C$_3$-C$_6$-alkenyl, C$_3$-C$_6$-alkynyl or C$_7$-C$_{10}$-arylalkyl, X- is a plant-tolerated anion, and n is 0 or 1, or plant-tolerated salts thereof.

2. A fungicidal composition containing a fungicidally effective amount of a compound of claim 1 and an inert carrier.

3. A process for combating fungi, wherein the fungi or the materials, plants, seed or soil to be protected against fungus attack are treated with a fungicidally effective amount of a compound of claim 1.

4. N-Substituted 3-arylpyrrolidine derivatives of the formula I

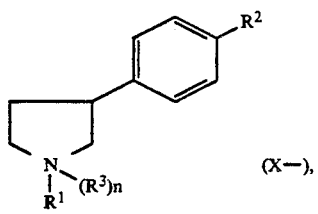

(I)

where

R¹ is $C_3$-$C_9$-trialkylsilyl-substituted $C_4$-$C_{12}$-cycloalkyl or unsubstituted or hydroxy-, $C_1$-$C_9$-alkyl-, $C_1$-$C_5$-alkoxy- or $C_3$-$C_9$-trialkylsilyl-substituted $C_5$-$C_{12}$-cycloalkenyl, R¹ is further $C_9$-$C_{11}$-bicycloalkyl which is unsubstituted or substituted by hydroxy, $C_1$-$C_6$-alkyl, $C_1$-$C_5$-alkoxy, $C_3$-$C_9$-trialkylsilyl, acetoxy, benzoyloxy or benzyloxy, R¹ is further 4-tert.-butoxybenzyl, 1,4-dioxaspiro[4,5]decan-8-yl, 5 to 7-membered heterocycloalkyl having 1 or 2 heteroatoms selected from the group consisting of oxygen and sulfur, 5 to 7-membered heterocycloalkylmethyl having 1 or 2 heteroatoms selected from the group consisting of oxygen and sulfur, $C_1$-$C_8$-alkyl-substituted 5 to 7-membered heterocycloalkyl or heterocycloalkylmethyl having 1 or 2 heteroatoms selected from the group consisting of oxygen and sulfur, R² is $C_3$-$C_{10}$-alkyl, $C_3$-$C_8$-alkoxy or $C_3$-$C_9$-trialkylsilyl, R³ is $C_1$-$C_5$-alkyl, $C_3$-$C_6$-alkenyl, $C_3$-$C_6$-alkynyl or $C_7$-$C_{10}$-arylalkyl, X- is a plant-tolerated anion, and n is 0 or 1, or plant-tolerated salts thereof.

5. A fungicidal composition containing a fungicidally effective amount of a compound of claim 4 and an inert carrier.

6. A process for combating fungi, wherein the fungi or the materials, plants, seed or soil to be protected against fungus attack are treated with a fungicidally effective amount of a compound of claim 4.

7. N-Substituted 3-arylpyrrolidine derivatives of the formula I

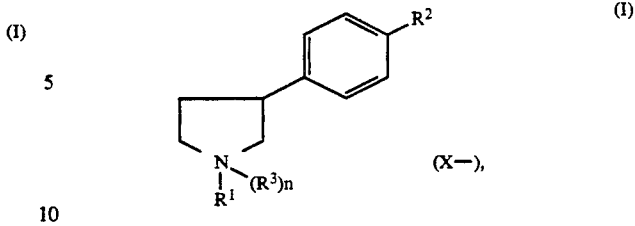

(I)

where

R¹ is 2,2-dimethylpropyl, 3,3-dimethylbutyl, 4,4-dimethylpentyl, 2,4,4-trimethylpentyl, 6-methylhept-2-yl, 3,5,5-trimethylhexyl, 6,10-dimethylundec-2-yl, 3-methylcyclohexyl, 3,3-dimethylcyclohexyl, 3,3,5-trimethylcyclohexyl, 3,3,5,5-tetramethylcyclohexyl, 4-methylcyclohexyl, 4-ethylcyclohexyl, 4-propylcyclohexyl, 4-isopropylcyclohexyl, 4-tert.-butylcyclohexyl, 4-(2-methylbut-2-yl)cyclohexyl, 4-(2,4,4-trimethylpent-2-yl)cyclohexyl, cyclododecanyl, $C_3$-$C_9$-trialkylsilyl-substituted $C_4$-$C_{12}$-cycloalkyl, 4-hydroxycyclohexyl, 4-hydroxy-3-methylcyclohexyl, 4-hydroxy-3,5-dimethylcyclohexyl, 4-hydroxy-3,3-dimethylcyclohexyl, 4-hydroxy-3,3,5-trimethylcyclohexyl, unsubstituted or hydroxy-, $C_1$-$C_9$-alkyl-, $C_1$-$C_5$-alkoxy- or $C_3$-$C_9$-trialkylsilyl-substituted $C_5$-$C_{12}$-cycloalkenyl, R¹ is further $C_9$-$C_{11}$-bicycloalkyl which is unsubstituted or substituted by hydroxy, $C_1$-$C_6$-alkyl, $C_1$-$C_5$-alkoxy, $C_3$-$C_9$-trialkylsilyl, acetoxy, benzoyloxy or benzyloxy, R¹ is further 4-tert.-butyl-benzyl, 4-chlorobenzyl, 4-tert.-butoxybenzyl, 1,4-dioxaspiro[4,5]decan-8-yl, 5 to 7-membered heterocycloalkyl having 1 or 2 heteroatoms selected from the group consisting of oxygen and sulfur, 5 to 7-membered heterocycloalkylmethyl having 1 or 2 heteroatoms selected from the group consisting of oxygen and sulfur, $C_1$-$C_8$-alkyl-substituted 5 to 7-membered heterocycloalkyl or heterocycloalkylmethyl having 1 or 2 heteroatoms selected from the group consisting of oxygen and sulfur, R² is $C_3$-$C_{10}$-alkyl, $C_3$-$C_8$-alkoxy or $C_3$-$C_9$-trialkylsilyl, R³ is $C_1$-$C_5$-alkyl, $C_3$-$C_6$-alkenyl, $C_3$-$C_6$-alkynyl or $C_7$-$C_{10}$-arylalkyl, X- is a plant-tolerated anion, and n is 1, or a plant-tolerated salt thereof.

8. A fungicidal composition containing a fungicidally effective amount of a compound of claim 7 and an inert carrier.

9. A process for combating fungi, wherein the fungi or the materials, plants, seed or soil to be protected against fungus attack are treated with a fungicidally effective amount of a compound of claim 7.

10. N-(2-Decalyl)-3-(4-tert-butylphenyl)-pyrrolidine.

11. N-(4,4-Dimethylpentyl)-3-(4-tert-butylphenyl)-pyrrolidine.

* * * * *